(12) United States Patent
Kehoe

(10) Patent No.: US 11,246,584 B2
(45) Date of Patent: Feb. 15, 2022

(54) ALL-SUTURE ANCHOR AND DEPLOYMENT ASSEMBLY

(71) Applicant: CONMED Corporation, Utica, NY (US)

(72) Inventor: Thomas Kehoe, Tarpon Springs, FL (US)

(73) Assignee: CONMED Corporation, Utica, NY (US)

( * ) Notice: Subject to any disclaimer, the term of this patent is extended or adjusted under 35 U.S.C. 154(b) by 168 days.

(21) Appl. No.: 16/362,742

(22) Filed: Mar. 25, 2019

(65) Prior Publication Data

US 2019/0290256 A1    Sep. 26, 2019

Related U.S. Application Data

(60) Provisional application No. 62/647,874, filed on Mar. 26, 2018, provisional application No. 62/646,983, filed on Mar. 23, 2018, provisional application No. 62/646,963, filed on Mar. 23, 2018.

(51) Int. Cl.
*A61B 17/04* (2006.01)

(52) U.S. Cl.
CPC .. *A61B 17/0401* (2013.01); *A61B 2017/0409* (2013.01); *A61B 2017/0464* (2013.01)

(58) Field of Classification Search
CPC .......... A61B 17/0401; A61B 17/06166; A61B 17/0057; A61B 2017/0406; A61B 2017/0414; A61B 2017/0446; A61B 2017/0448; A61B 2017/0459; A61B 2017/0464; A61B 2017/042; A61B 2017/06185; A61F 2/0811; A61F 2002/0852
USPC ........................................................ 606/232
See application file for complete search history.

(56) References Cited

U.S. PATENT DOCUMENTS

| | | | | |
|---|---|---|---|---|
| 2011/0208239 A1* | 8/2011 | Stone | ................. | A61B 17/0485 606/228 |
| 2012/0197271 A1* | 8/2012 | Astorino | ............ | A61B 17/0057 606/148 |
| 2014/0039503 A1* | 2/2014 | Pilgeram | ............ | A61B 17/0482 606/80 |
| 2014/0257383 A1* | 9/2014 | Lombardo | ......... | A61B 17/0401 606/232 |

\* cited by examiner

*Primary Examiner* — Melanie R Tyson
(74) *Attorney, Agent, or Firm* — Bond, Schoeneck & King, PLLC; Frederick J. M. Price

(57) ABSTRACT

An all-suture anchor for attaching soft tissue to bone while creating an interference fit within a bone hole, and a deployment device for the all-suture anchor. The all-suture anchor includes an anchor body having first and second ends. The second end is folded toward the first end, creating a looped distal end of the anchor body, while the first and second ends of the anchor body form a proximal end. The anchor body is composed of a first material having a first density. A passing filament, of a second (different) density, is woven through the anchor body at passing locations such that a pair of free ends of the passing filament extends from the proximal end of the anchor body. The all-suture anchor additionally includes a binding filament bound axially at the proximal end of the anchor body around the first end and the second end of the anchor body.

8 Claims, 35 Drawing Sheets

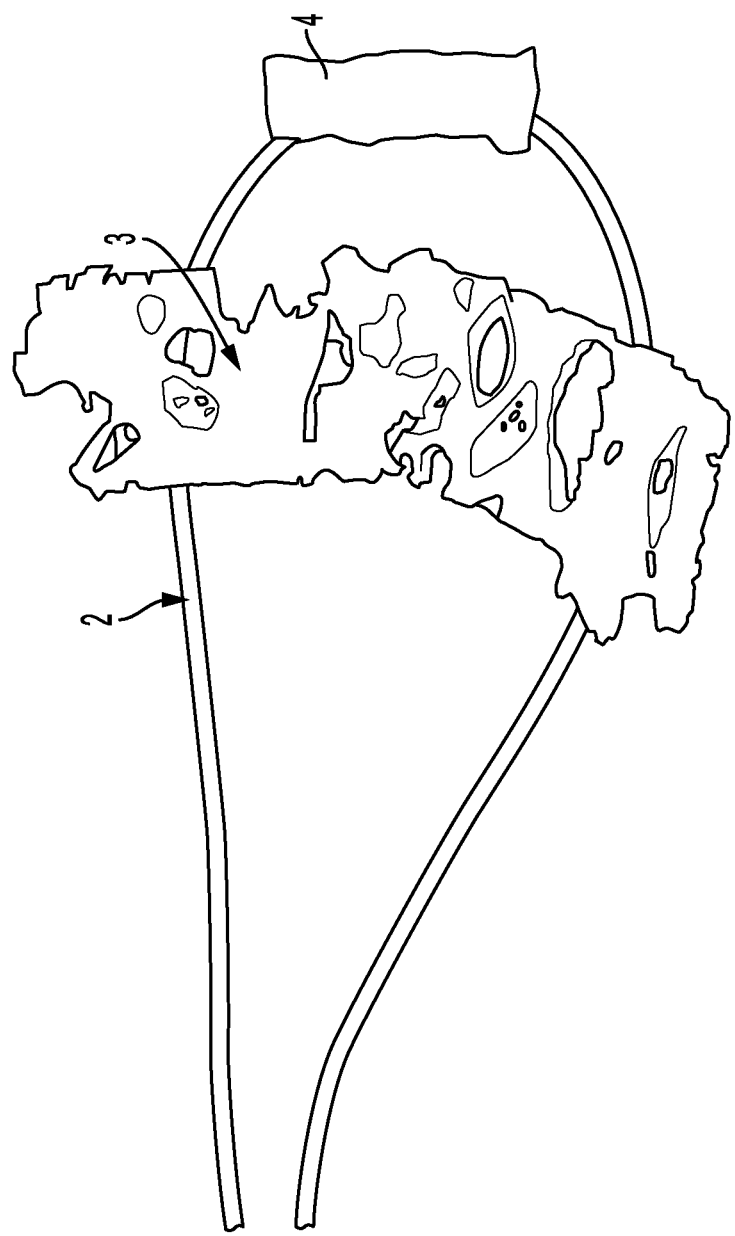

ALL-SUTURE ANCHOR AND DEPLOYMENT ASSEMBLY

CROSS-REFERENCE TO RELATED APPLICATIONS

This application claims priority to U.S. Provisional Patent Application Ser. No. 62/646,963 filed on Mar. 23, 2018 and entitled "Multi-Density, Non-Uniform All Suture Anchor," U.S. Provisional Patent Application Ser. No. 62/646,983 filed on Mar. 23, 2018 and entitled "Segmented All Suture Anchor," and U.S. Provisional Patent Application Ser. No. 62/647,874, filed on Mar. 26, 2018 and entitled "Rigid Body Anchor with All-Suture Deployment Mechanism," the entireties of which are incorporated herein by reference.

BACKGROUND OF THE INVENTION

1. Field of the Invention

The present invention is directed generally to an all-suture anchor and, more particularly, to a multi-density all-suture anchor and deployment device.

2. Description of Related Art

Current rigid body expanding anchors used in arthroscopy to attach soft tissue to bone are typically larger in size as compared to soft, all-suture anchors. In contrast, the all-suture anchors are typically smaller in size, yet oftentimes do not provide the fixation strength of larger, rigid body anchors when used in soft bone. Furthermore, the current rigid body expanding anchors consist of two rigid body members that must be actuated until an internal mechanism controlled by distance is reached. When used in hard bone, there exists instances where the interference fit between anchor and bone is so great after insertion, that an anchor expansion mechanism fails to deploy.

Hand set deployment of arthroscopic all-suture anchors pull out of hard and soft bone more readily than all-suture anchors deployed by a driver/inserter mechanism. A typical driver/inserter mechanism consists of a method for deploying an all-suture anchor against a rigid body within the hole prepared in bone by the surgeon. Currently, all-suture anchors that are used to re-attach soft tissue to bone consist of a single material and contain a uniform density. This homogenous suture anchor structure is relatively smooth and soft in nature, allowing it to more easily be pulled out of uniform densities of hard and soft bone where no sub-cortical bone shelf exists.

Therefore, there is a need for a soft suture anchor that can have an interference fit within a bone hole, and a deployment device therefor that does not need to reach a particular deployment distance.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

The present invention is directed to an all-suture anchor for attaching soft tissue to bone while creating an interference fit within a bone hole, and a deployment device for the all-suture anchor. According to one aspect, the all-suture anchor includes an anchor body having a first end and a second end. The second end is folded toward the first end, creating a looped distal end of the anchor body. The first end and the second end of the anchor body form a proximal end of the anchor body. The anchor body is composed of a first material having a first density. The all-suture anchor also includes a passing filament having a pair of free ends. The passing filament is woven through the anchor body at a plurality of passing locations such that the pair of free ends extends from the proximal end of the anchor body. The passing filament is composed of a second material having a second density, and the second density is different than the first density. The all-suture anchor additionally includes a binding filament bound axially at the proximal end of the anchor body around the first end and the second end of the anchor body.

According to another aspect, the all-suture anchor includes an anchor body having a first end and a second end. The second end is folded toward the first end, creating a first limb extending to the first end and a second limb extending to the second end. The anchor body is composed of a first material having a first density. The all-suture anchor also includes a first piercing (or hole) in the second limb and the first limb extends through the first piercing. The all-suture anchor additionally includes a passing filament having a pair of free ends. The passing filament is woven through the anchor body at a plurality of passing locations such that one of the pair of free ends extends from the first end of the anchor body and the other of the pair of free ends extends from the second end of the anchor body. The passing filament is composed of a second material having a second density, and the second density is different than the first density.

According to another aspect, the present invention is a suture anchor deployment assembly. The assembly includes: (i) a suture anchor deployment device having a tube with a channel extending therethrough and (ii) a suture anchor. The suture anchor includes an anchor body having a proximal end and a distal end. The anchor body composed of a first material having a first density. The suture anchor also includes a passing filament having a pair of free ends. The passing filament is woven through the anchor body at a plurality of passing locations such that the pair of free ends extends from the proximal end of the anchor body. The passing filament is composed of a second material having a second density, and the second density is different than the first density. The anchor body is positioned within the tube of the suture anchor deployment device such that the pair of free ends of the passing filament extends proximally from the tube. In an undeployed state, the tube has a first diameter and in a deployed state, the tube has a second diameter which is greater than the first diameter.

In one or more embodiments briefly described above (and further described below), the first and second densities can be the same or similar.

Embodiments of the all-suture anchors described herein can include a fibrous construct anchor body portion (or fibrous, braided or woven fabric-type structure such as a flexible web), and a suture or filament portion having a first end and a second end. The anchor body can be hollow, cored, tubular or nontubular, and/or flat. The suture can pass through the anchor body in a number of ways (including woven, pass through a column, pierced through top and bottom, etc., as should be understood by a person of ordinary skill in the art in conjunction with a review of this disclosure). The anchor body can include a first state in which the anchor body is uncompressed and extends along the longitudinal axis of the suture when in an unfolded and pre-deployed condition; and a second state in which the flat anchor body is compressed and expanded in a direction perpendicular to longitudinal axis of the suture in a deployed condition (as discussed herein).

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

FIG. 35 is a side view digital photograph of an embodiment of the woven material of FIG. 31 in a post-deployment configuration after addition of an activator.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
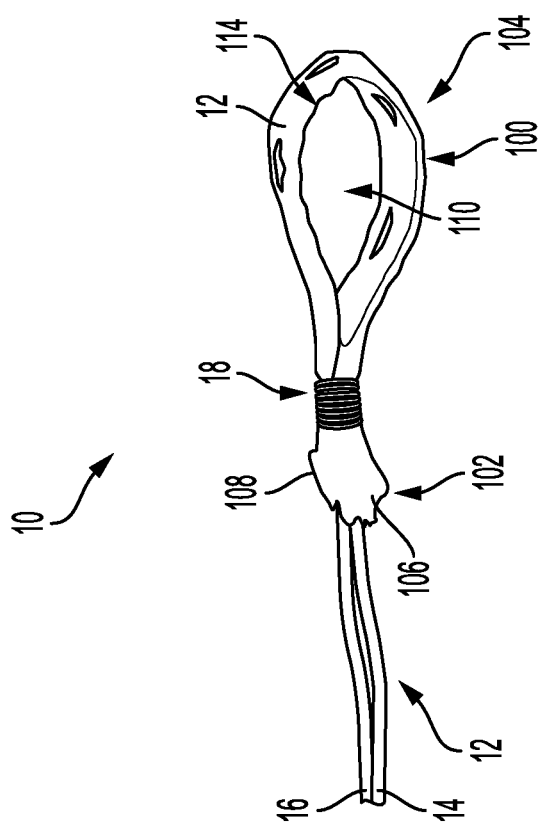
FIG. 1 is a side view schematic representation of a dual density all-suture anchor in an undeployed state, according to an embodiment.

Referring now to the figures, wherein like reference numerals refer to like parts throughout, FIG. 1 shows a side view schematic representation of a dual density all-suture anchor 10 in the undeployed state, according to an embodiment. The anchor 10 comprises a braided anchor body 100, which is folded to form a proximal or first end 102 and a looped distal or second end 104. In the depicted embodiment, the braided anchor body 100 is a length of suture braid with a first end or limb 106 and a second end or limb 108. The second end 108 has been folded to the first end 106, creating a loop 110 in the braided anchor body 100. In an embodiment, the anchor body 100 is composed of an ultra-high-molecular-weight polyethylene (UHMWPE) braid. Nevertheless, the anchor body 100 has a first density. The anchor body 100 can be flat, tubular, hollow tubular, or of any other known geometry.

Figure 2:
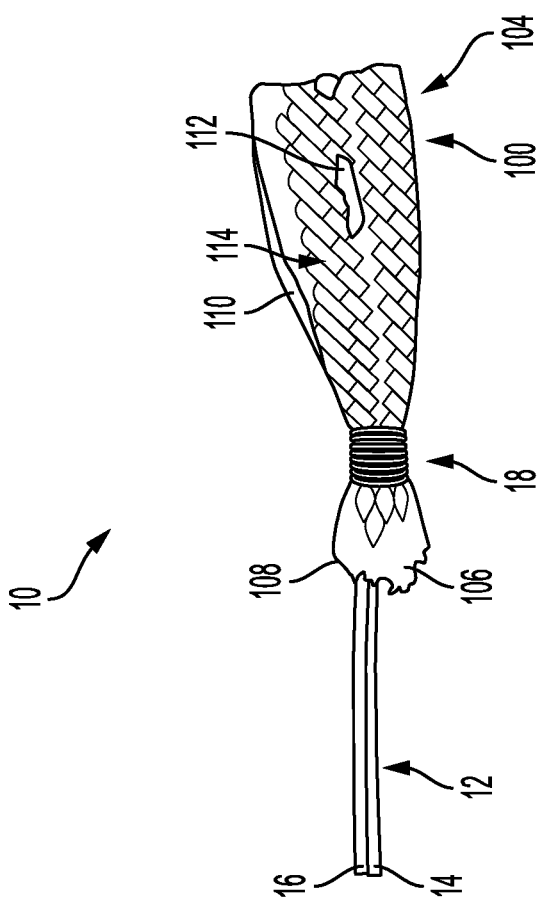
FIG. 2 is a top view schematic representation of a dual density all-suture anchor in an undeployed state, according to an embodiment.

Turning now to FIG. 2, there is shown a top view schematic representation of the dual density all-suture anchor 100 in the undeployed state, according to an embodiment. As shown in FIG. 2, the anchor 10 additionally comprises a passing filament 12 woven through the anchor body 100 at a plurality of passing locations 112. The passing filament 12 is woven through the anchor body 100 such that free ends 14, 16 of the passing filament 12 extend from the proximal end 102 of the anchor body 100. The passing filament 12 may be woven through the anchor body 100 prior to or after folding the second end 108 to the first end 106. In addition, the passing filament 12 is woven such that one or more passing sections 112 of the passing filament 12 are exposed on an outer surface 114 of the anchor body 100, as shown in FIG. 2.

Still referring to FIG. 2, the passing filament 12 is composed of a material having a second density. The second density of the passing filament 12 is different from the first density of the anchor body 100. Thus, the passing filament 12 adds irregularity to the anchor body 100 and creates an additional form of fixation by creating irregularity against/within a bone hole surface. Additional anchor locking occurs through interdigitation of the passing filament 12 and anchor body 100 and the creation of rigid mechanism "barbs" on the exterior surface 114 of the anchor body 100.

As shown in FIGS. 1 and 2, the anchor body 100 is bound axially at the proximal end 102 with multiple passes of a binding filament 18 (e.g., monofilament) through the proximal end 102 of the anchor body 100. The binding filament 18 is passed around and/or through the proximal end 102 of the anchor body 100, simulating a binding sleeve around the proximal end 102. In the depicted embodiment, the proximal end 102 is bound such that the first and second ends 106, 108 of the anchor body 100 extend proximally from the binding filament 18. The proximal end 102 can be bound by other biocompatable material, which can include tape and other like materials (as should be understood by a person of ordinary skill in the art in conjunction with a review of this disclosure).

The addition of the binding filament 18 to the anchor 100 in FIGS. 1 and 2 provides an interference fit with surface of the bone hole because the binding filament 18 acts as a rigid body at the proximal end 102 of the anchor 100. This allows the distal end 104 of the anchor body 100 to have a semi-rigid shoulder to expand against when the anchor 10 is deployed. The addition of binding filament 12 at the proximal end 102 of the anchor body 100 also provides a semi-rigid body that occludes the prepared anchor hole (i.e., bone hole), allowing the distal end 104 of the anchor body 100 to expand and gain additional purchase in hard and soft bone compared to single material/density all suture anchors.

Figure 3:
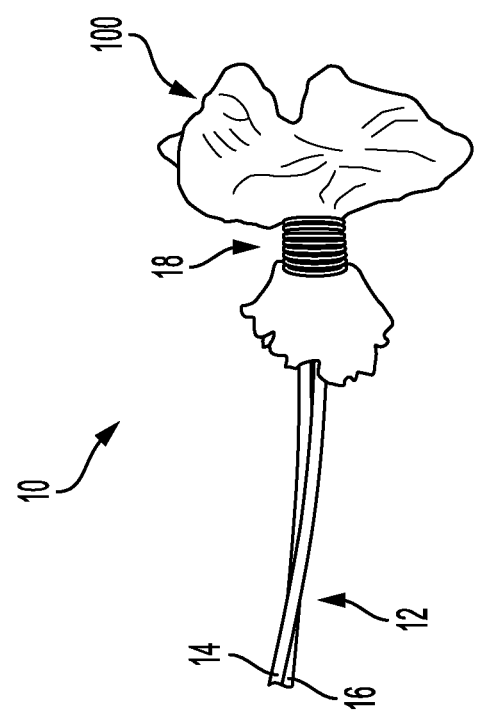
FIG. 3 is a side view schematic representation of a dual density all-suture anchor in a deployed state, according to an embodiment.

From the undeployed state shown in FIGS. 1 and 2, the anchor 10 is inserted into a bone hole for deployment. Once the anchor 10 is placed within the bone hole (not shown), the user (e.g., surgeon) deploys the anchor 10 by tensioning the free ends 14, 16 of the passing filament 12. The anchor 10 can be deployed with the aid of an inserter (not shown) or any other known device used to deploy all-suture anchors, e.g., U.S. Pat. No. 9,173,652 (as should be understood by a person of ordinary skill in the art in conjunction with a review of this disclosure). When the passing filament 12 is tensioned, the anchor body 100 expands to the deployed state, shown in FIG. 3. The free ends 14, 16 of the passing filament 12 can then be used to secure soft tissue in apposition to the bone comprising the bone hole. In particular, the free ends 14, 16 of the passing filament 12 can be used to secure the soft tissue in apposition to the bone with one or more knots.

Figure 4:
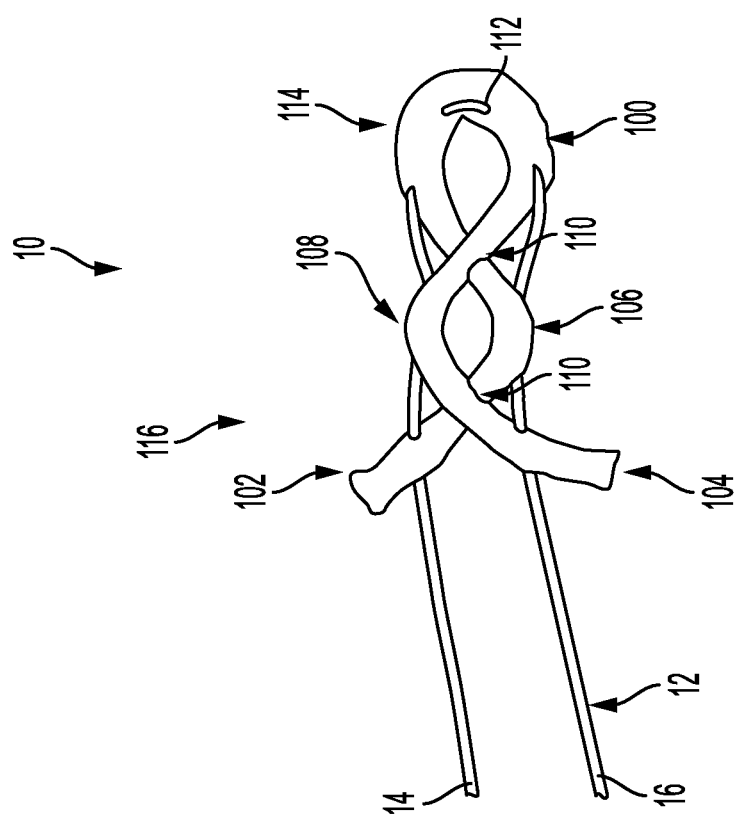
FIG. 4 is a side view schematic representation of a round anchor body in an undeployed state, according to an alternative embodiment.

Turning now to FIGS. 4-7, there is shown various views schematic representations of an all-suture anchor 10, according to an alternative embodiment. The all-suture anchor 10 in FIGS. 4-7 is comprised of uniform density material that is pierced upon itself one or more times to achieve contrasting densities in strategic locations. For example, FIG. 4 shows a side view schematic representation of a round anchor body 100, in the undeployed state, which has been pierced and passed through itself. In the embodiment shown in FIG. 4, the anchor body 100 has a first end 102 and a second end 104, and has been folded at some point therebetween, creating a first limb 106 extending to the first end 102 and a second limb 108 extending to the second end 104.

The first limb 106 comprises at least one piercing 110 (or hole) and/or the second limb 108 comprises at least one piercing 110. In the embodiment depicted in FIG. 4, the second limb 108 comprises two piercings 110 along its length. The first limb 106 is then passed through both piercings 110 in the second limb 108, creating the "figure 8" shape in the anchor body 100, as shown in FIG. 4. In an alternative embodiment, in FIG. 5, there is shown a side view schematic representation of a flat anchor body 100 in the undeployed state. In the depicted embodiment, the second limb 108 of the anchor body 100 comprises one piercing 110 and the first limb 106 is passed through the one piercing 110 in the second limb 108.

Figure 5:
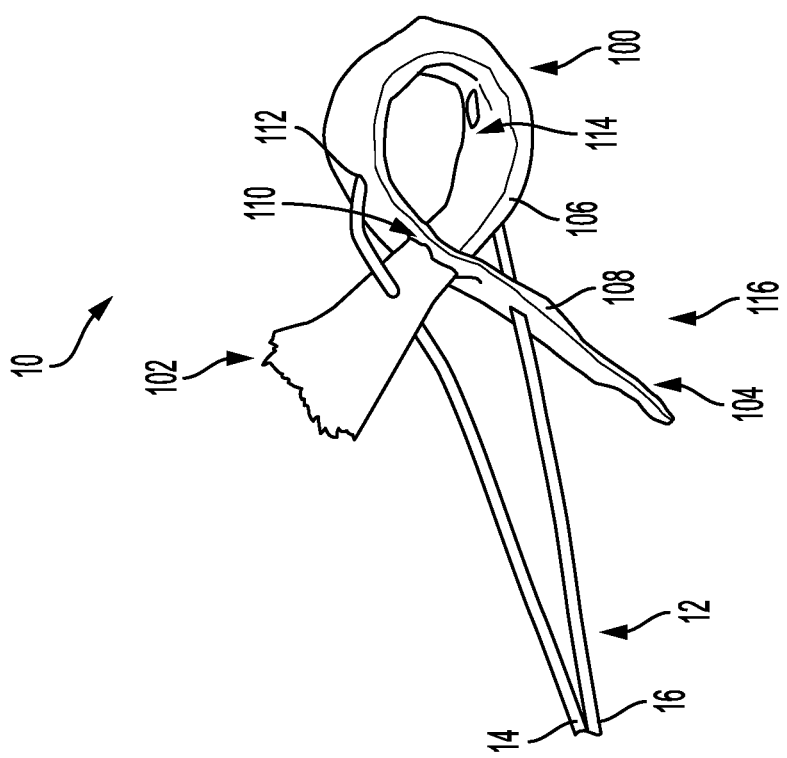
FIG. 5 is a side view schematic representation of a flat anchor body in an undeployed state, according to an alternative embodiment.

In both of the exemplary embodiments shown in FIGS. 4 and 5, a passing filament 12 is passed through the anchor body 100 after the first or second limbs 106, 108 have been passed through the each other as described above. The passing filament 12 is woven through multiple passing locations 112 along the anchor body 100. In FIGS. 4 and 5, the passing filament 12 is woven through the first end 102 and then the second limb 108 and a distal loop 114 of the anchor body 100 before it is woven through passing locations 112 along the first limb 106 and the second end 104. Ultimately, the passing filament 12 is woven through the anchor body 100 in a "U-shaped" pattern such that free ends 14, 16 of the passing filament 12 extend proximally from a proximal end 102 of the anchor body 100. The free ends 14, 16 of the passing filament are used to secure soft tissue in apposition to the bone comprising the bone hole after the anchor 10 is deployed in the bone hole.

Figure 6:
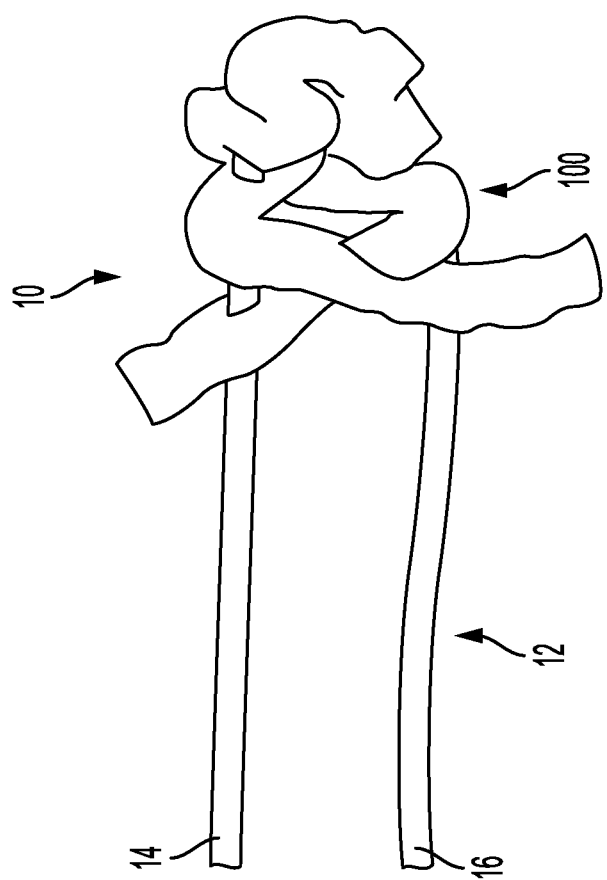
FIG. 6 is a side view schematic representation of the round anchor body in FIG. 4 in a deployed state.
Figure 7:
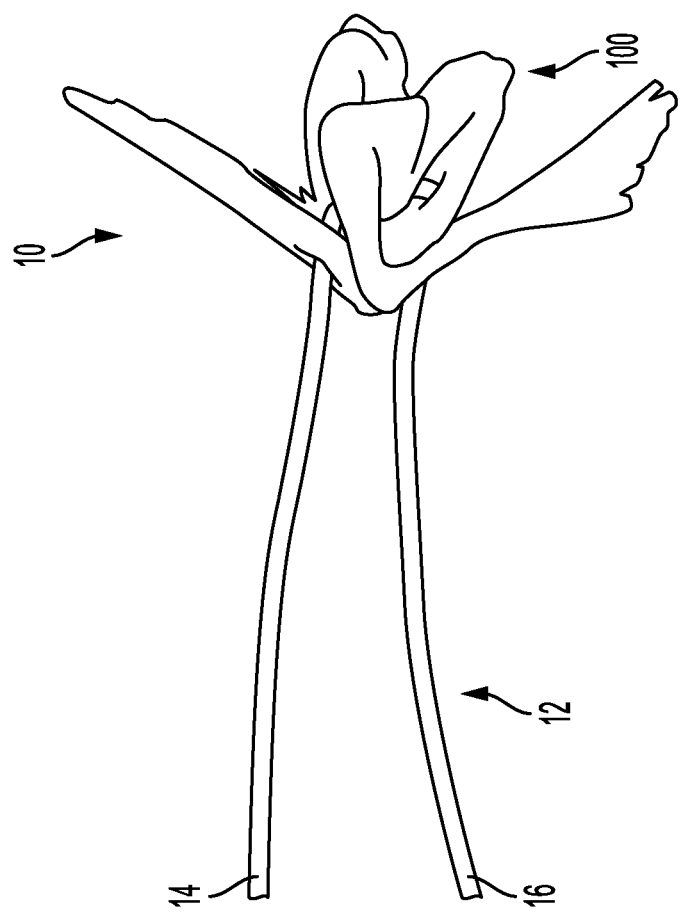
FIG. 7 is a side view schematic representation of the flat anchor body in FIG. 5 in a deployed state.

Referring now to FIGS. 6 and 7, there are shown various views schematic representations of the all-suture anchor 10 in the deployed state, according to an alternative embodiment. From the undeployed state shown in FIGS. 4 and 5, the anchor 10 is inserted into a bone hole (not shown) for deployment. Once the anchor 10 is placed within the bone hole, the user (e.g., surgeon) deploys the anchor 10 by tensioning the free ends 14, 16 of the passing filament 12. The anchor 10 can be deployed with the aid of an inserter (not shown) or any other known device used to deploy conventional suture anchors (see reference above). When the passing filament 12 is tensioned, the anchor body 100 expands to the deployed state, shown in FIGS. 6 and 7. The free ends 14, 16 of the passing filament 12 can then be used to secure soft tissue in apposition to the bone comprising the bone hole. In particular, the free ends 14, 16 of the passing filament 12 can be used to secure the soft tissue to the bone with one or more knots.

The passing filament 12 and particular "piercing" configuration anchor body 100 of in FIGS. 4-7 creates contrasting densities with single uniformed material based anchor body 100. This all-suture anchor 10 generates compression against bone in the pierced, high material density locations (i.e., where there are piercings 110), and anchor expansion in the low material density locations (i.e., where there are no piercings 110). This creates intended, segmented areas of expansion (or alternating zones of press-fit fixation and anchor expansion) as if a chain of anchors were deployed in sequence. Further, the all-suture anchor 10 generates interference fixation in bone prior to anchor deployment that is not achieved by current commercialized all-suture anchors that can, under certain circumstances, pull out of a bone hole while being deployed.

Figure 8:
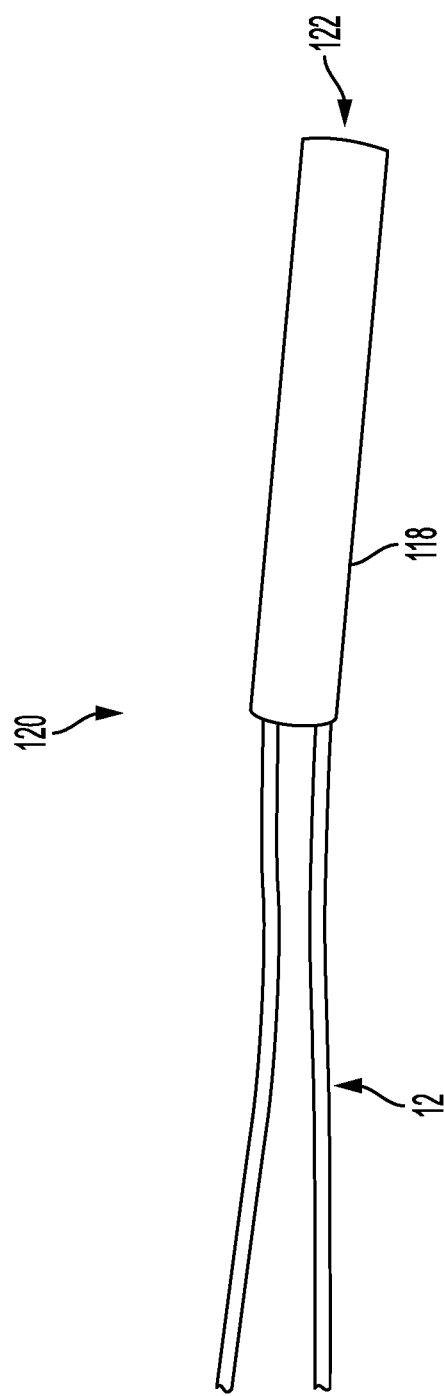
FIG. 8 is a perspective view schematic representation of a suture deployment device in a pre-deployment configuration, according to an embodiment.

Turning now to FIG. 8, there is shown a perspective view schematic representation of a suture deployment device 120 in a pre-deployment configuration, according to an embodiment. The suture deployment device 120 comprises a tube 118 with a channel 122 extending therethrough. The tube 118 can be composed of a polymer, such as PEEK, bio composite, or the like. Preferably, the tube 118 is thin such that it expands easily when pressure is applied the inside surface by an expanding anchor positioned therein upon deployment.

Still referring to FIG. 8, the channel 122 is sized and configured to contain an anchor 10 therein. The anchor 10 can be the all-suture anchors 10 shown in FIGS. 1-7. The anchor 10 may also be any known anchor, such as a rigid body anchor, a soft anchor, or an all-suture anchor, for example. The anchor 10, in an undeployed state, is inserted into the channel 122 of the suture deployment device 120. Sutures or other passing filaments 12 connected to the anchor 10 remain outside the suture deployment device 120, as shown. With the anchor 10 in the undeployed state and loaded in the suture deployment device 120, the suture deployment device 120 is inserted (e.g., tapped) into a bone hole for deployment.

Figure 9:
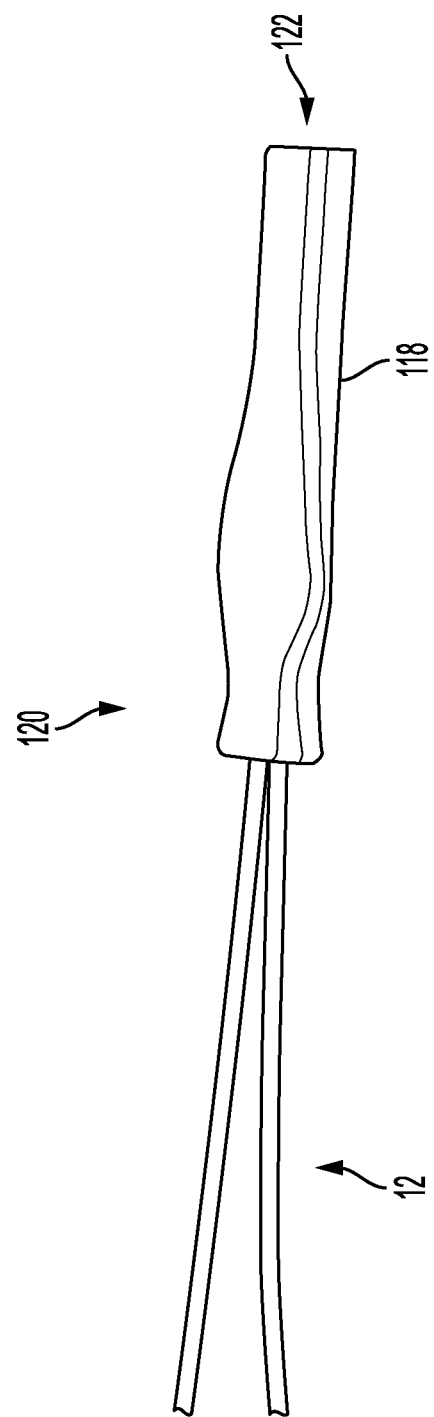
FIG. 9 is a perspective view schematic representation of a suture deployment device in a deployed configuration, according to an embodiment.

Referring now to FIG. 9, there is shown a perspective view schematic representation of the suture deployment device 120 in a deployed configuration, according to an embodiment. Once the suture deployment device 120 is placed within the bone hole (not shown), the user (e.g., surgeon) deploys the anchor 10 by actuating an inserter (not shown) or any other similar device (as referenced above). The act of deployment causes the anchor body 100 of the anchor 10 to be drawn distally, shortening in length while expanding radially. Specifically, the expansion of the anchor body 100 causes the tube 118 to expand against the walls of the bone hole. In other words, the tube 118 has a first diameter in the undeployed state and a second diameter in the deployed state due to the expansion of the anchor body 100 positioned therein. The deployed anchor body 100 is locked into the expanded tube 118 via internal features, such as ribs or threads in the tube 118. This allows the expansion mechanism to deploy without the need of a minimum travel distance as in the case of predicate two-piece rigid body expanding anchors. Ribs, threads, teeth or other surface features can be included on the outside surface of the tube 118 to assist with locking the deployed deployment device 120 in place.

Although the suture deployment device 120 in FIGS. 8 and 9 can be used to with the expanding soft suture anchors 10 in FIGS. 1-7, the suture deployment device 120 can also be used with any expanding soft suture anchor, including any of the following expanding soft suture anchors (as should be understood by a person of ordinary skill in the art in conjunction with a review of this disclosure).

Turning now to FIGS. 10-35, there are shown various views schematic representations of a woven material (or soft anchor) 100, according to a multitude of embodiments, which can be used in conjunction with the suture deployment device 120 described herein above. Generally, the following described and illustrated alternative all-suture anchor designs are configured to work with and be deployed (and expand in a deployed state) by the suture deployment device 120 described herein in the same manner as the woven material 100 and other all-suture anchors, described and illustrated herein. These alternative all-suture anchor design embodiments, and related functionalities are described separately below.

Figure 10:
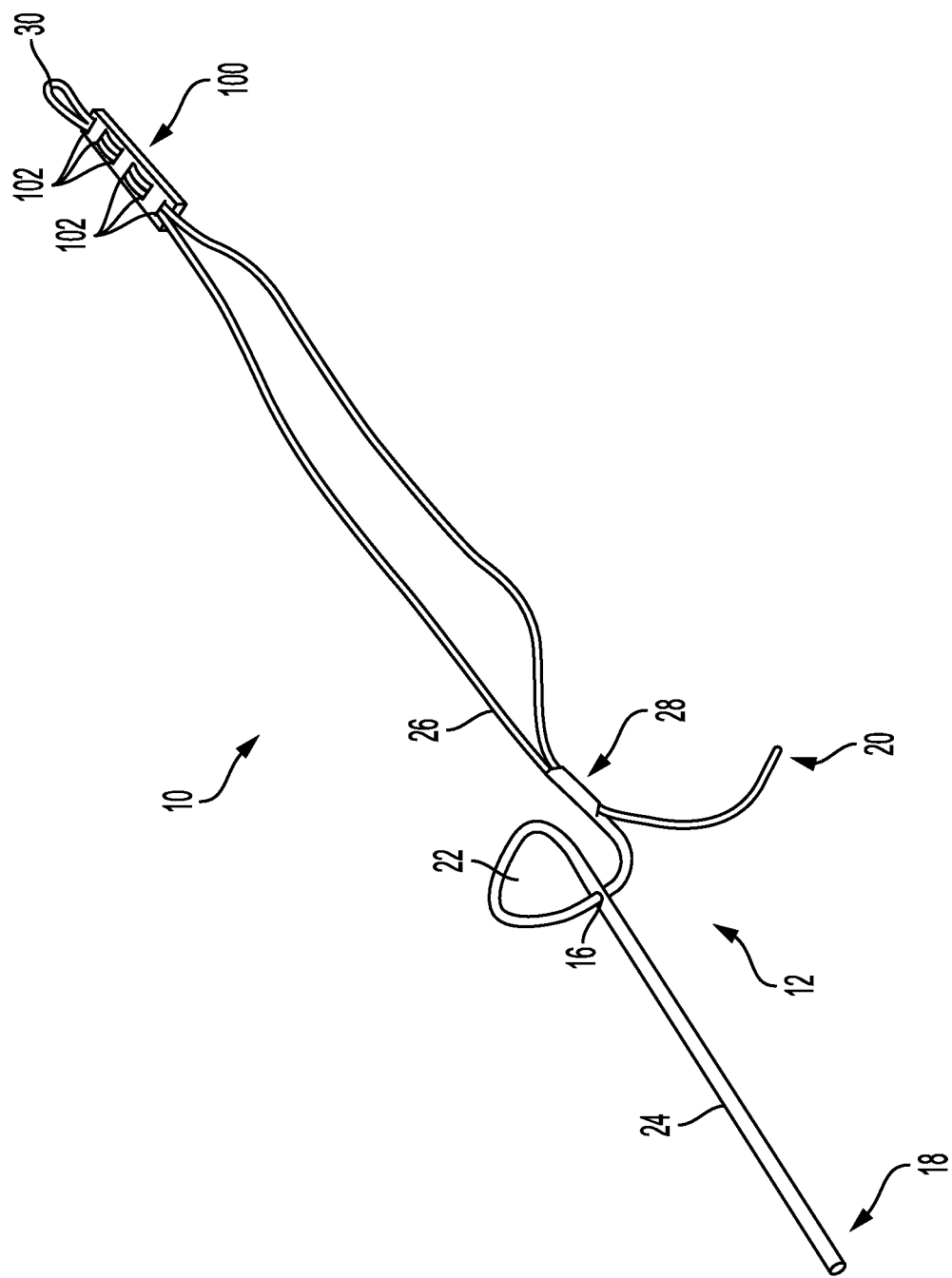
FIG. 10 is a perspective view schematic representation of a knotless instability anchor in a pre-deployment configuration, according to another embodiment.

FIG. 10 shows a perspective view schematic representation of a knotless instability anchor 10 in a pre-deployment configuration, according to another embodiment. The knotless instability anchor 10 includes a woven material (anchor) 100 and a strand of suture (or "suture strand") 12. To achieve the anchor 10 in FIG. 10, a pierce (or aperture) 16 is first formed at or near a first end 18 of the suture strand 12. A second end 20 of the suture strand 12 is passed through the pierce 16, creating a self-collapsing loop 22 with a first limb 24 and a second limb 26 of the suture strand 12 extending therefrom. The second end 20 is pulled through the pierce 16 and away from the first end 18. A splice 28 is then created in the second limb 26 of the suture strand 12. As also shown in FIG. 10, the second end 20 of the suture strand 12 is pulled through the splice 28, creating an adjustable loop 30 in the second limb 26 of the suture strand 12. As shown in FIG. 10, the adjustable loop 30 is pulled through a woven material 100 which functions as a soft all-suture anchor (e.g., Y-Knot anchor). The anchor 10 in FIG. 10 is deployed using the adjustable loop 30 and the self-collapsing loop 22, as shown and described in PCT Patent Application No. PCT/US18/61168 (as should be understood by a person of ordinary skill in the art in conjunction with a review of this disclosure).

Figure 11:
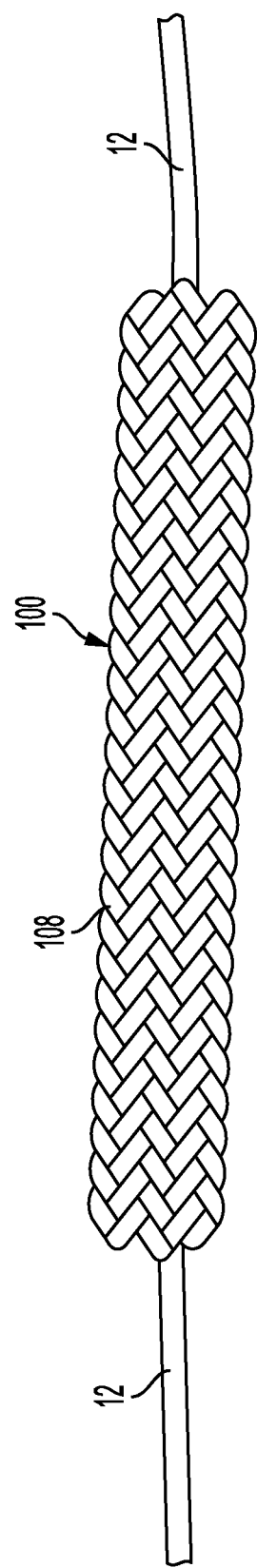
FIG. 11 is a back view schematic representation of a woven material, according to an alternative embodiment.
Figure 12:
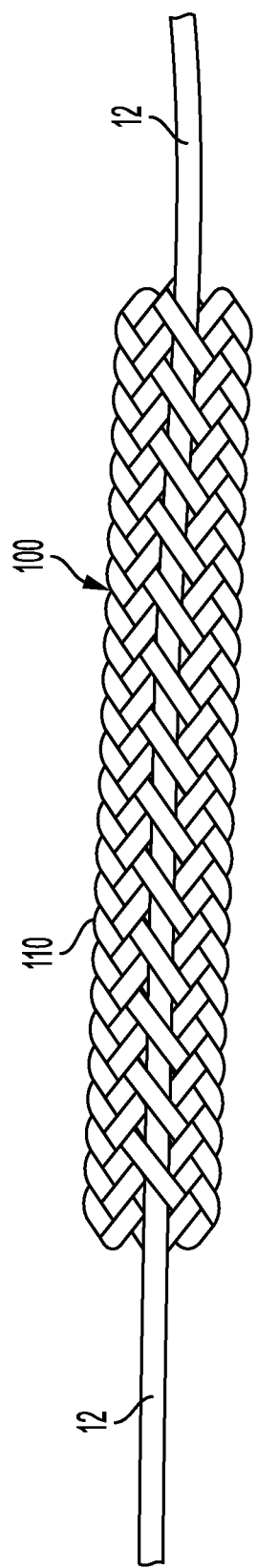
FIG. 12 is a top view schematic representation of the woven material of FIG. 11.

Referring briefly to FIGS. 11-14, there are shown front and back views schematic representations of a woven material 100, according to an embodiment. In FIGS. 11-14, the woven material 100 is an all-suture anchor braid. FIG. 11 shows a back view of an all-suture anchor 100, while FIG. 12 shows the front view. As shown, the length of suture 12 passing into and out of the woven material (i.e., anchor braid/fibrous construct) 100 only passes through one (e.g., "front") surface 110 of the anchor braid 100 (FIG. 12).

Figure 13:
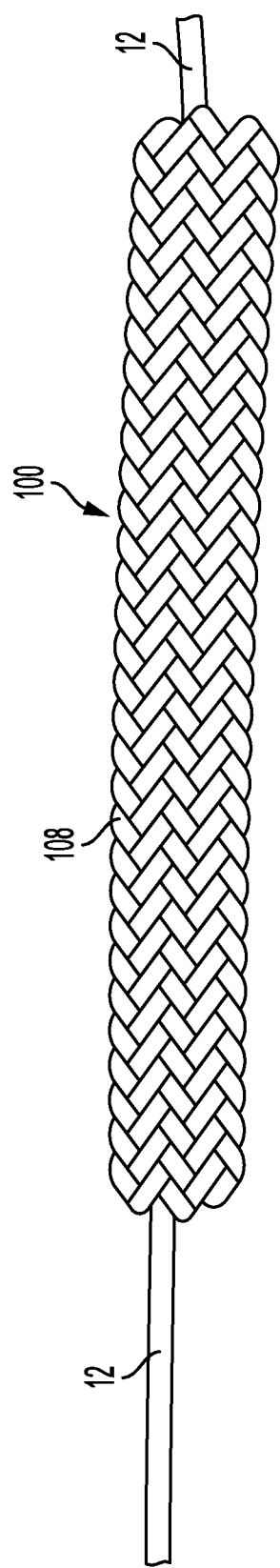
FIG. 13 is a back view schematic representation of a woven material, according to an alternative embodiment.
Figure 14:
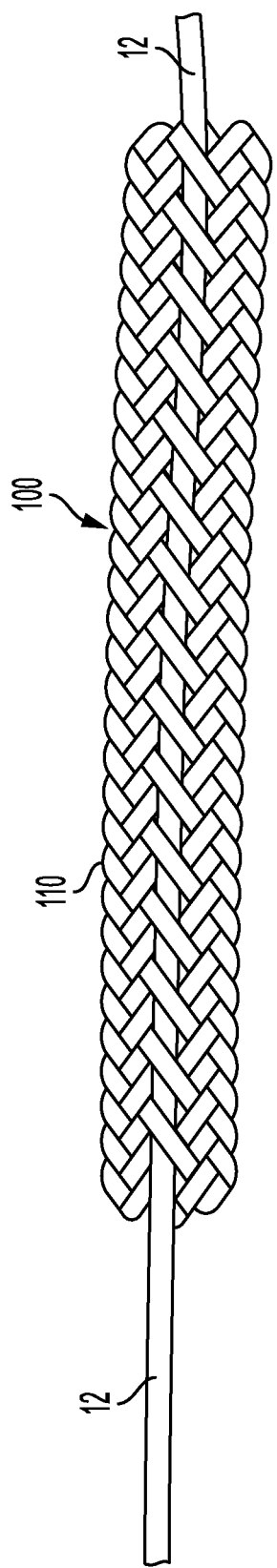
FIG. 14 is a top view schematic representation of the woven material of FIG. 13.
Figure 17:
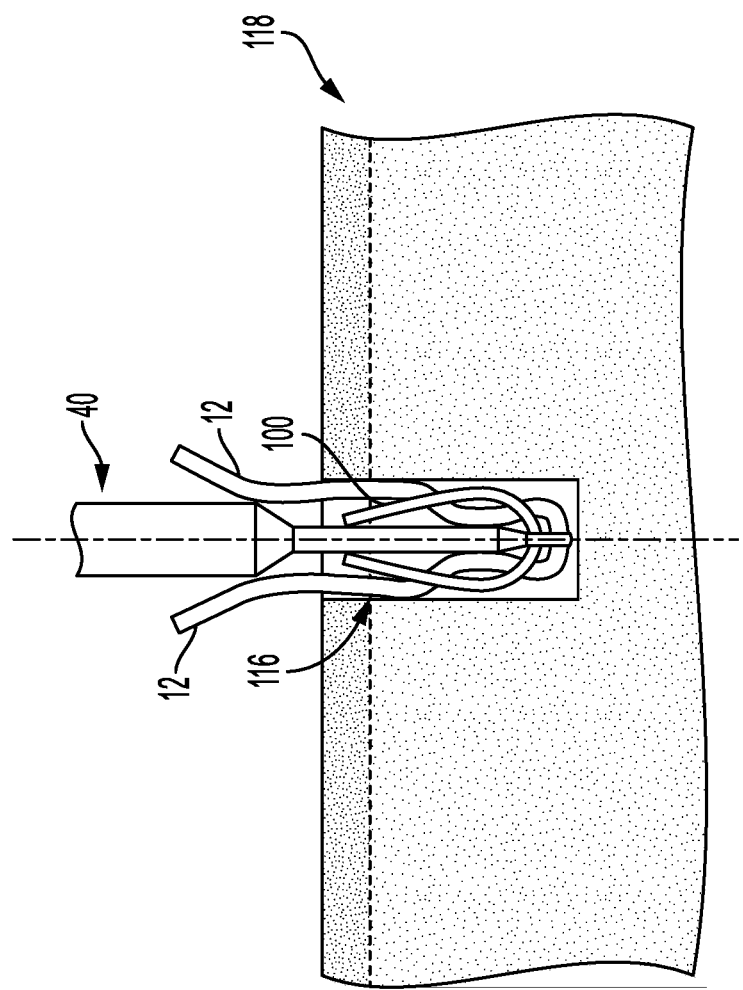
FIG. 17 is a side view schematic representation of an embodiment of a woven material in the undeployed state, according to an alternative embodiment.

Similarly, FIGS. 13-14 also show a back view (FIG. 14) and front view (FIG. 13) where the suture 102 passing only through one (e.g., "front") surface 110 of the anchor braid 100 (FIG. 14). When the all-suture anchor 100 has suture 12 passing only through one (e.g., "front") surface 110, the anchor braid 100 protects the suture 12 from abrasion on the opposing (e.g., "back") surface 108 (FIGS. 11 and 13) when loaded onto a driver (e.g., driver 40 as shown in FIG. 17) (as should be understood by a person of ordinary skill in the art in conjunction with a review of this disclosure). In FIGS. 11-14, the suture 12 is passed through the anchor braid 100 at numerous passing locations. In an embodiment, the number of passing locations is eight passing locations, while the number of passing locations for some alternative all-suture anchors 100 is six passing locations. The number of passing locations can vary depending on the composition and size of the suture 12 and/or anchor braid 100. The number of passing locations can be optimized by balancing input parameters, such as anchor braid length, anchor braid width, anchor braid pick density, suture diameter, and others, to yield output parameters, such as manufacturability, anchor creep under load, and pullout strength.

Figure 15:
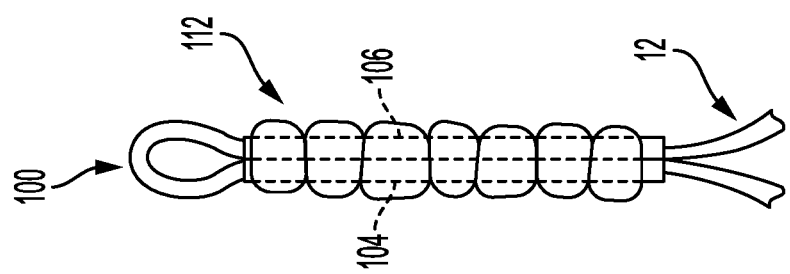
FIG. 15 is a top view schematic representation of a woven material folded and stitched, according to an embodiment.
Figure 16:
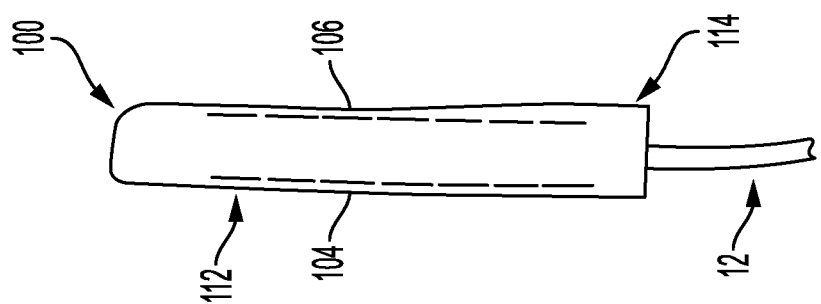
FIG. 16 a top view schematic representation of a woven material of FIG. 15 with an additional material covering.

Turning now to FIGS. 15-16, there are shown top views schematic representations of an alternative embodiment of a woven material 100. In FIGS. 15-16 the woven material 100 is an anchor braid 100 with an additional material 112. One of ordinary skill in the art should recognize and appreciate potential embodiments of a Y-Knot® anchor with additional material, such as monofilament polymers, to add strength. Additional material 112 can be applied to the all-suture anchor 100. As shown in FIG. 15, the anchor braid 100 is folded in half. A monofilament 112 is used to stitch together each (i.e., two) side edge 104, 106 of the anchor braid 100 to create an enclosed area 114 with the length of suture 12 inside, as shown in FIG. 16. In addition to improved strength, this will prevent the anchor braid 100 from rolling over on itself during insertion and exposing the suture 12 to the bone, causing abrasion. Additionally, the described twisting of the anchor braid 100, in combination with a more dense material running in the axis of the anchor braid 100 can result in a threaded all-suture anchor 100.

Figure 18:
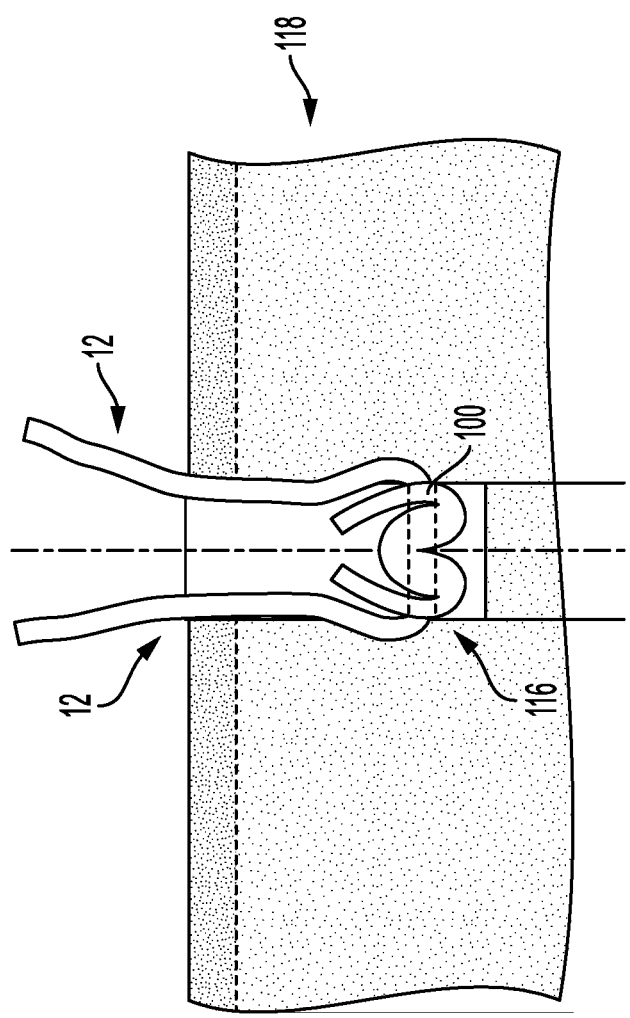
FIG. 18 is a side view schematic representation of the woven material of FIG. 17 shortened and expanded in the deployed state, according to an alternative embodiment.

Turning now to FIGS. 17-18, there are shown side view schematic representations of an embodiment of an alternative embodiment of a woven material 100 in the pre-deployment and post-deployment configurations. In the depicted embodiment, the woven material 100 is a soft all-suture anchor, such as the Y-Knot® anchor. One such suture anchor is disclosed in U.S. Pat. No. 9,826,971 assigned to the assignee hereof and incorporated by reference herein in its entirety.

An embodiment of the Y-Knot® anchor (or soft anchor or "all-suture" anchor) 100 is illustrated in detail in FIGS. 17-18. The Y-Knot® anchor 100, as shown in FIGS. 17-18, contains at least two sections: at least one suture 12, which is a suture to be anchored; and an anchor body 100 (e.g., fibrous construct, as should be understood by those of ordinary skill in the art in conjunction with a review of this disclosure), which is to form a portion of the anchor 100 that can increase in width, thickness and/or diameter and shrink in length as part of deployment. See FIG. 17, showing the anchor body 100 in the pre-deployment configuration; and FIG. 18, showing the anchor body 100 "shortened" and "expanded" in the post-deployment configuration, which is additive to the increase due to the pleats. This soft anchor embodiment also takes advantage of Poisson's ratio, which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body 100 that increases in width, thickness and/or diameter at deployment, it should be understood that the suture 12 can also play a role in the deployment of the anchor 100 even though the suture 12 may remain free (in some embodiments) to slide, and non-slidable in others (at least at a particular position or point in use) in relation to the anchor body 100. The suture 12 helps to position, align and support the anchor body 100, such that if the suture 12 were to be removed from the anchor body 100 after deployment of the anchor 100, the anchor body 100 may be free to spill (i.e., release), allowing the anchor body 100 to collapse and shrink in size, allowing for easy (and potentially undesirable) removal.

In other words, the anchor body 100 has two primary functions. First, it becomes a base for the suture 12 to slide within. Second, when compressed and/or pleated during deployment, the anchor body 100 becomes more compact in one direction thereby expanding outwardly and increasing its overall width, thickness or diameter to create a retention capacity. This action of having the anchor body 100 change in shape to increase its overall width, thickness or diameter is a useful characteristic which may be used advantageously to secure the anchor 100 in a hole 116 or against a bony or soft tissue 118. It is this combination of the expanding anchor body 100 coupled with the suture 12 remaining slidable (in some embodiments; and non-slidable in others, at least at a particular position or point in use) in relation to the anchor body 100 that render embodiments of the present invention ideal for the reattachment of soft tissue to bone 118 or soft tissue to soft tissue where it is desirable to pass sliding knots to secure a repair.

Figure 19:
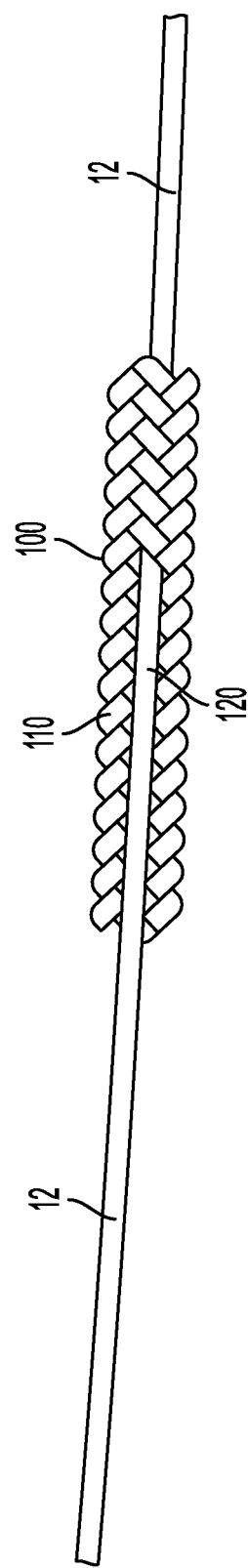
FIG. 19 is a top view schematic representation of an woven material, according to an alternative embodiment.
Figure 20:
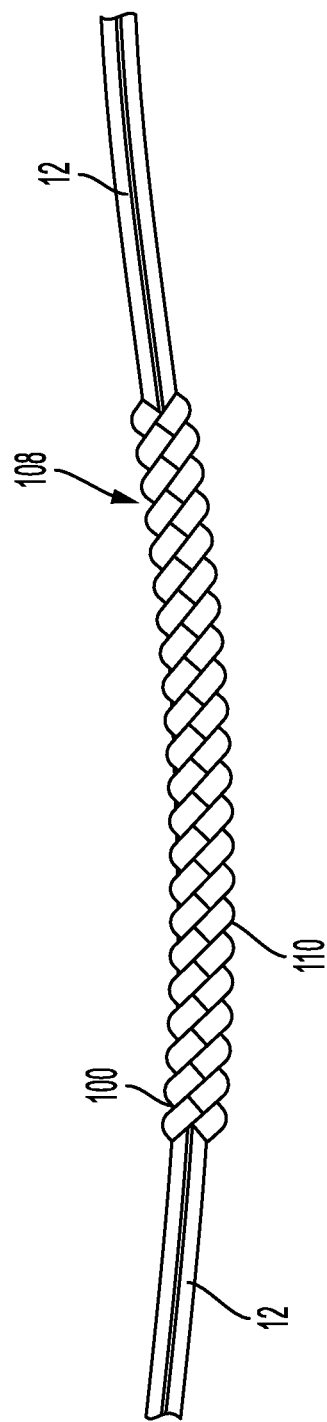
FIG. 20 is a side view schematic representation of the woven material in FIG. 19.

Turning briefly to FIGS. 19-20, there are shown top and side views schematic representations of a woven material 100, according to an alternative embodiment. In FIGS. 19-20 the woven material 100 is an all-suture anchor braid. As shown in FIGS. 19-20, the length of suture 12 passes through an approximate center 120 of the anchor braid 100. In the depicted embodiment, the length of suture 12 enters the anchor braid 100 through one (e.g., "front") surface 110 and exits through the opposing (e.g., "back") surface 108 of the anchor braid 100. With the length of suture 12 positioned on both sides of the anchor braid 100, the anchor braid 100 can be loaded onto the driver 40 (see FIG. 17) such that anchor braid 100 can be positioned against a bone, while the lengths of suture 12 are along the driver 40.

Figure 21:
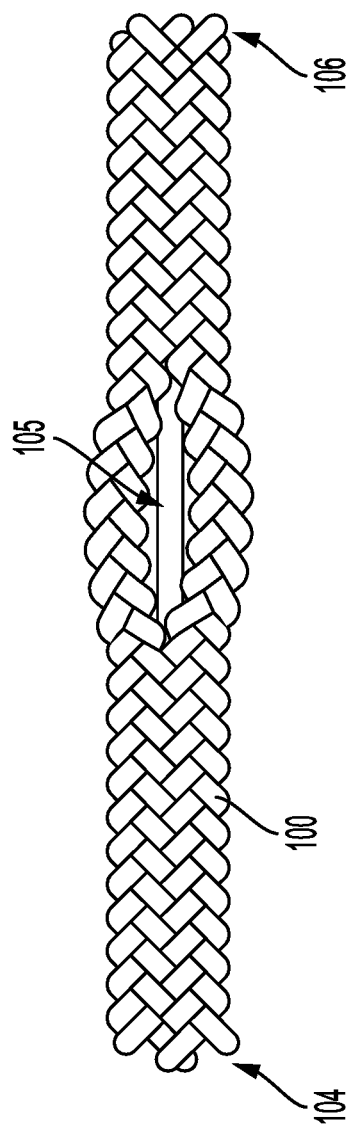
FIG. 21 is a top view schematic representation of a woven material with a central eyelet, according to an alternative embodiment.
Figure 22:
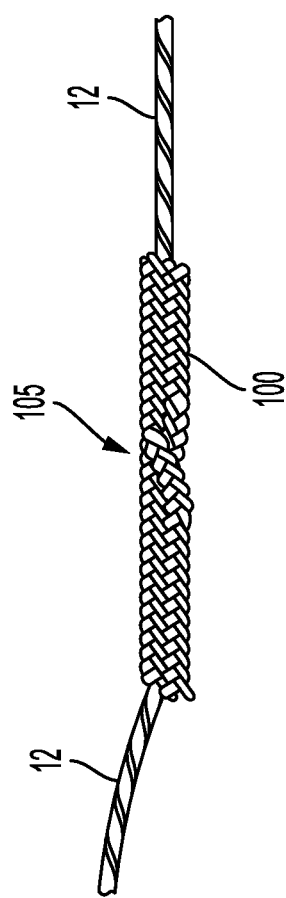
FIG. 22 is a top view schematic representation of the woven material of FIG. 21 with a length of suture passing through the central eyelet.

Referring now to FIGS. 21-22, there are shown top views schematic representations of a woven material 100, according an additional alternative embodiment. In FIGS. 21-22, the woven material 100 is an all-suture inverted anchor braid 100. To create an inverted anchor braid 100, a threader with a threader loop is first passed through the anchor braid 100. Then, in an end of the anchor braid 100 is pulled through the threader loop. Finally, the threader loop is pulled back through the anchor braid 100, creating a central eyelet 105, as shown in FIG. 21. A length of suture 12 can be loaded onto the inverted anchor braid 100 by passing the length of suture 12 through the anchor braid 100, as described in conjunction with any of the embodiments herein, and passing through the central eyelet 105, as shown in FIG. 22.

Figure 23:
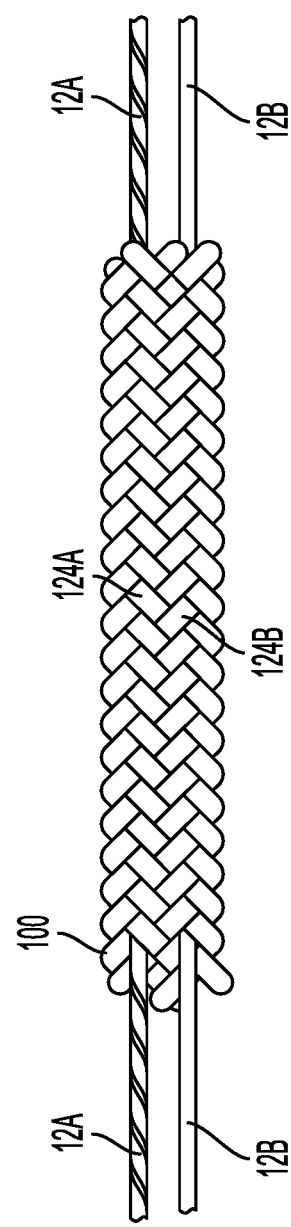
FIG. 23 is a top view schematic representation of a woven material loaded with two lengths of suture, according to an alternative embodiment.
Figure 24:
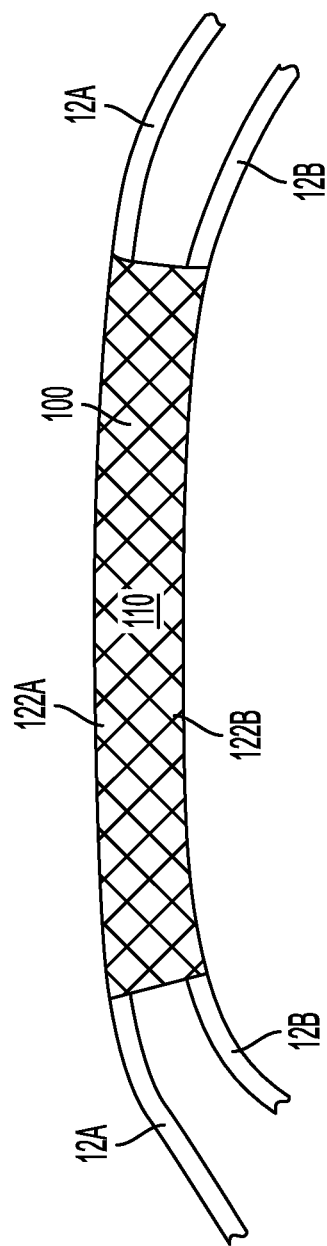
FIG. 24 is a top view schematic representation of a woven material loaded with two lengths of suture, according to an alternative embodiment.

In another alternative embodiment, as shown in FIGS. 23-24, the woven material 100 is an anchor braid 100 loaded with multiple lengths of suture 12A, 12B. In the depicted embodiment, the anchor braid 100 is loaded with two lengths of suture 12A, 12B. The lengths of suture 12A, 12B may extend through the anchor braid 100 along its opposing edges 122A, 122B (FIG. 24), through two off-center locations 124A, 124B (FIG. 23), or any conceivable combination thereof (including an extension of the length of suture 12A, 12B through the approximate center 120 of the anchor braid 100). In addition, the lengths of suture 12A, 12B may enter/exit the anchor braid 100 on the same surface (FIGS. 11-14) or on opposing surfaces (FIGS. 19-20).

Figure 25:
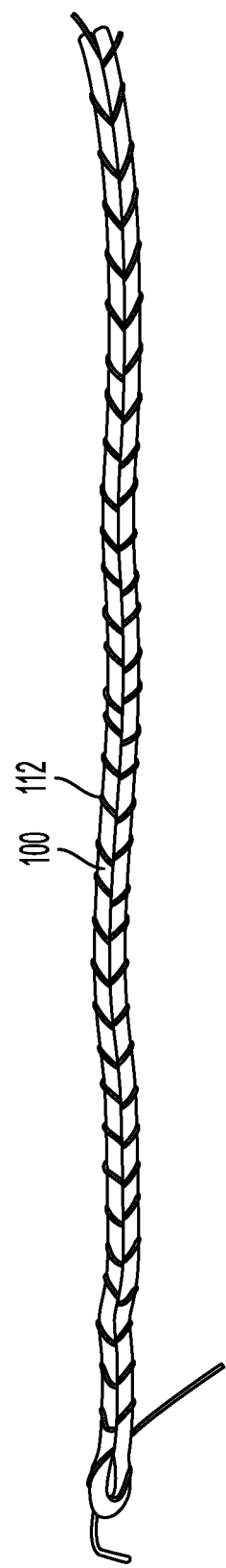
FIG. 25 is a top view schematic representation of a woven material with an additional monofilament, according to an alternative embodiment.
Figure 26:
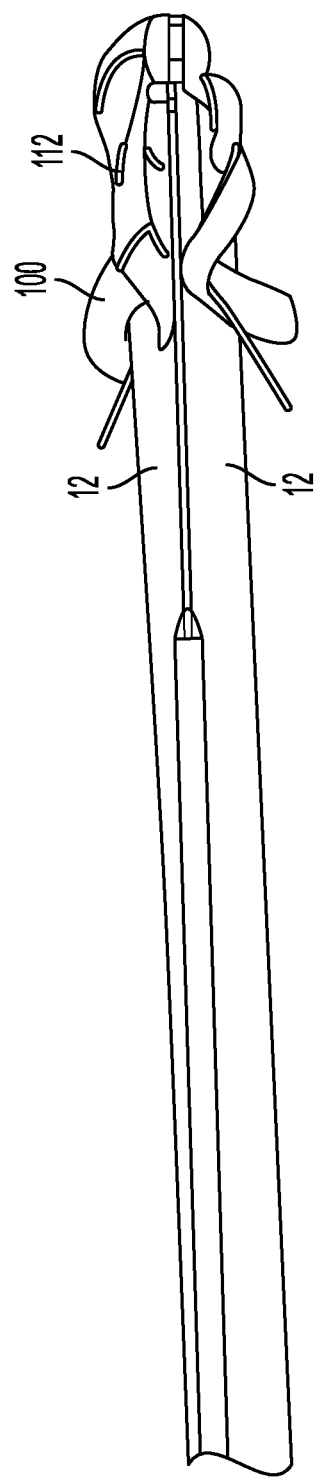
FIG. 26 is a side view schematic representation of the woven material of FIG. 25 loaded on an inserter (or driver)

In yet another alternative embodiment, as shown in FIGS. 25-26, the woven material 100 is an all-suture anchor comprised of flat braid, tube braid, cored suture, segmented suture of multiple densities, or suture with a contrasting density. The anchor 100 in FIGS. 25-26 includes an additional braided monofilament 112, for example. The additional braided monofilament 112 is woven around and through the anchor, as shown in FIG. 25. The additional braided monofilament 112 provides an additional form of fixation by creating irregularity within the bone surface via the added monofilament braid 112, additional anchor "locking" between the multi suture densities (interdigitation of monofilament co-mingled with UHMWPE braid locking/flipping) and/or the creation of rigid mechanical "barbs" on the exterior surface of the anchor 100 that are deployed via the base density of a UHMWPE braid. Lengths of suture (not shown) may enter/exit the anchor 100 as described above.

In accordance with another embodiment, the woven material 100 has an open elongated column/lumen extending from a first end to a second end; and the suture 12 passes through and is positioned at least partially in the open column. In an embodiment, the suture 12 is free to slide through the open column such that the suture 12 can be removed from the open column from the first end of the woven material 100 and the second end of the woven material 100. An embodiment of the woven material 100 can also be tubular in addition to having an open elongated column/lumen. The suture 12 may either be woven in situ directly onto the flat tape/woven material 100 (e.g., a round section suture braid), or woven with an open column into which the round section suture braid may be later inserted.

Figure 27:
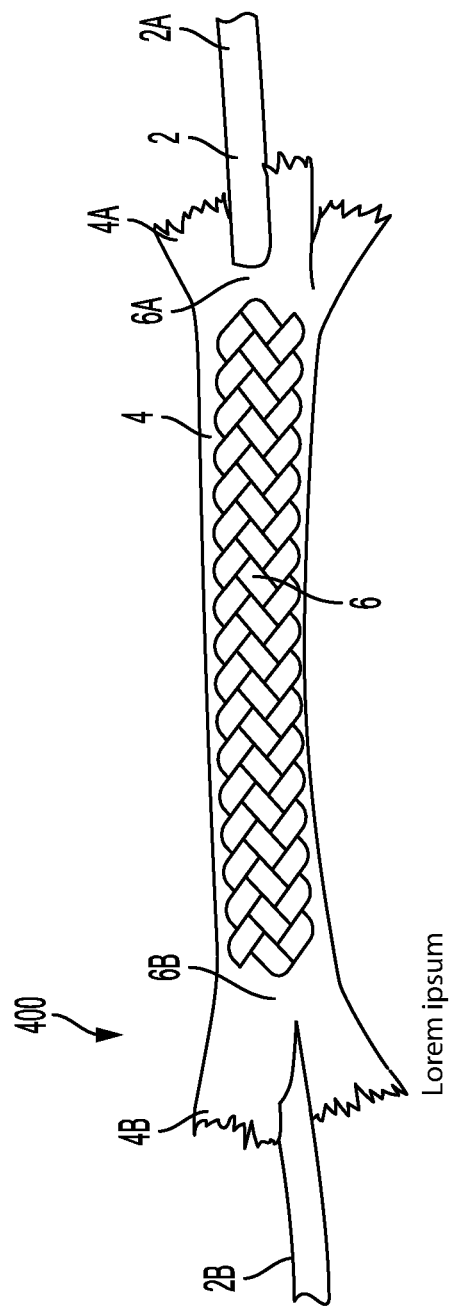
FIG. 27 is a perspective view digital photograph of a woven material in an unloaded (not loaded onto an installation device or inserter), pre-deployment configuration according to an alternative embodiment.

In particular, as seen in FIG. 27, a perspective view schematic representation of a woven material 400 in an unloaded (not loaded onto an installation device or inserter), pre-deployment configuration, according to an embodiment. In the depicted embodiment, the woven material 400 is a soft all-suture anchor. The all-suture anchor 400 can include, but is not limited to, a flat fibrous construct 4 having a first end 4A, a second end 4B, and an open elongated column/lumen 6 having a first end 6A and the second end 6B (each of the first end 6A and the second end 6B of the open elongated column/lumen 6 can extend between or beyond the first 4A and second 4B ends of the flat fibrous construct). The open elongated column/lumen 6 can be woven along an axis that is parallel to or along a central axis of the flat fibrous construct 4, or can be woven along a path that is not parallel to the central axis. As shown in FIG. 25, the open elongated column/lumen is woven along the central axis.

Still referring to FIG. 27, a filament 2 is shown having a first end 2A and a second end 2B, and passing through and at least partially positioned in the open column 6. In an embodiment, the filament 2 is free to slide through the open column 6 such that the filament 2 can be removed from the open column 6 from the first end 2A of the fibrous construct 2 and/or the second end 2B of the fibrous construct 2. In accordance with an alternative embodiment, the filament is locked and not slidable through the open column 6.

Figure 28:
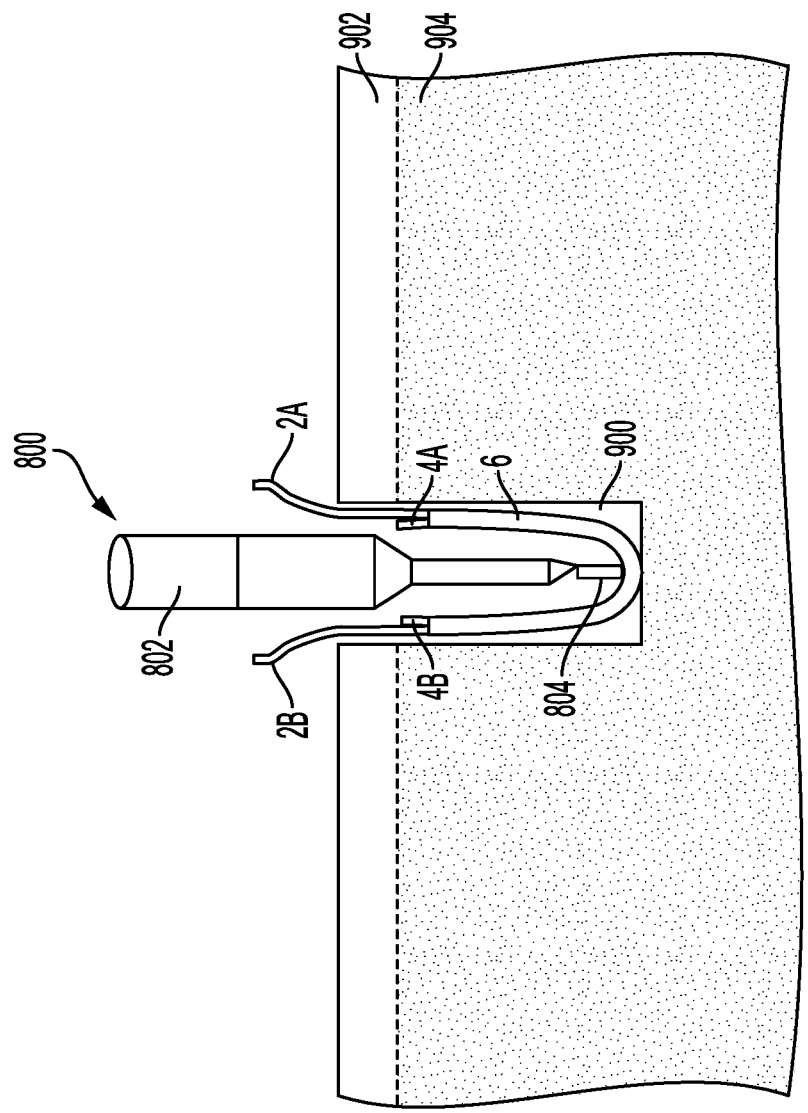
FIG. 28 is a side view schematic representation of an embodiment of the woven material of FIG. 27 connected to an installation device or inserter in a pre-deployment configuration.
Figure 29:
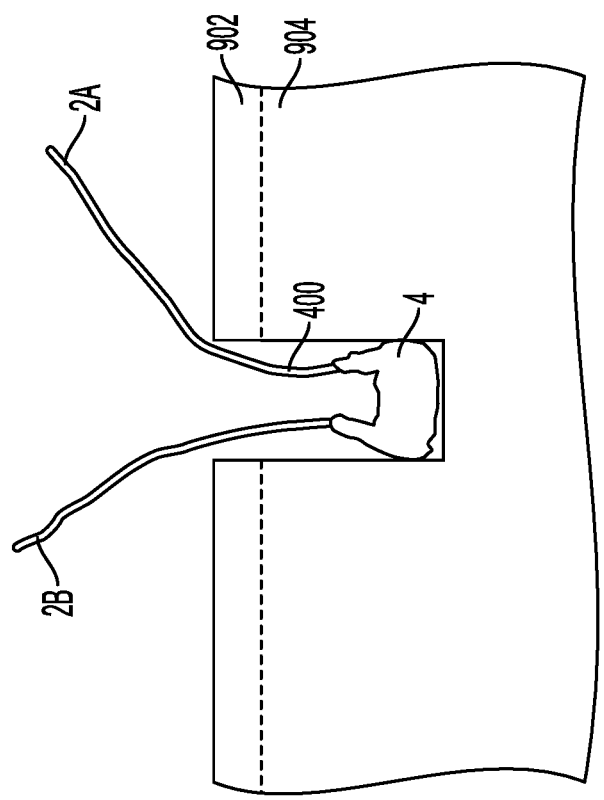
FIG. 29 is a side view schematic representation of an embodiment of the woven material of FIG. 27 in a post-deployment configuration positioned in a bone hole.
Figure 30:
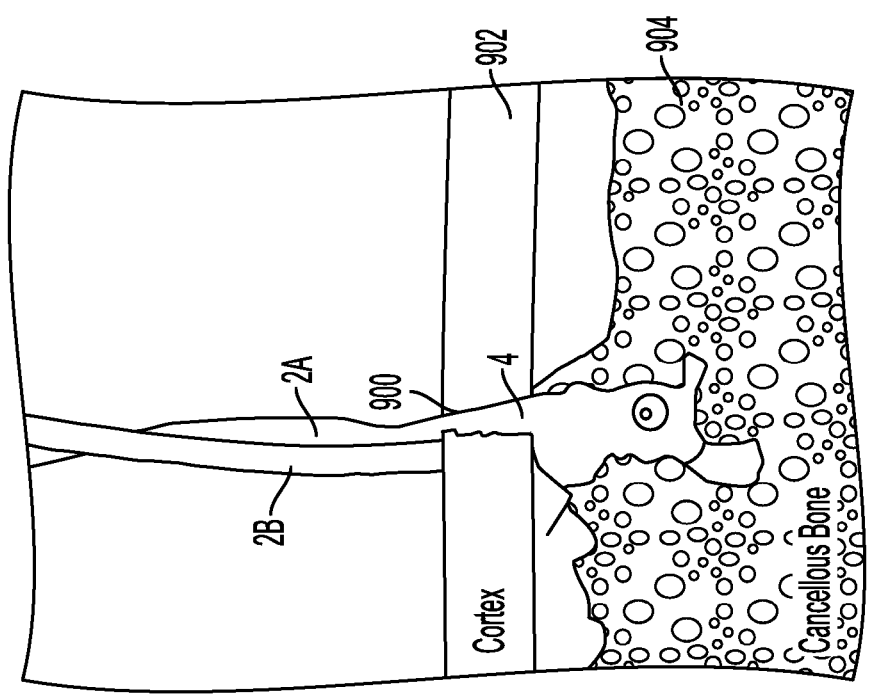
FIG. 30 is a side view digital photograph of an embodiment of the woven material of FIG. 27 in a post-deployment configuration positioned in a bone hole.

Turning now to FIGS. 28 and 29, there are shown side view schematic representations of an embodiment of the all-suture anchor 400 in the pre-deployment and post-deployment configurations. As described above, the all-suture anchor 400 contains at least two sections: at least one suture 2 with a first end 2A and a second end 2B; and an anchor body/fibrous construct 4 with a first end 4A and a second end 4B, and an open elongated column/lumen 6 extending from a first end 6A to a second end 6B, which is to form a portion of the anchor 400 that can increase in width, thickness and/or diameter and shrink in length as part of deployment.

As shown in FIG. 28, the installation device (or driver 40, as described herein above) in the pre-deployment configuration is provided. The all-suture anchor 400 is shown connected to the distal deployment end 804 of an installation device 800 (which can be a driver 40 of an embodiment described herein—see FIG. 17), which also includes a handle 802. The distal deployment end 804 and the all-suture anchor 100 are shown positioned in a bone hole 900 in cancellous bone 904 under the bone cortex 902. In order to deploy the all-suture anchor 400 (which can be connected to other tissue that needs to be brought into apposition to the bone, as should be understood by a person of ordinary skill in the art in conjunction with a review of this disclosure), the first end 2A and/or the second end 2B are pulled/tensioned in a direction away from the bone hole 400. The first end 2A and the second end 2B can be pulled/tensioned in a direction away from the bone hole 900 with or without the installation device 800 in place in the bone hole 900 (if installation device 800 is in place in the bone hole 900, it can act as a counter force to the tension force out of the hole 900 to assist with the deployment of the all-suture anchor 400).

As shown in FIG. 29, the anchor body/fibrous construct 4 is shown "shortened" and "expanded" in the post-deployment configuration and locked in the bone hole 900, which can be additive to the increase due to pleats formed by the fibrous construct 4 (which may also be part of the fibrous construct 4). See also FIG. 30. The all-suture anchor 400, and, in particular, the fibrous construct 4 takes advantage of Poisson's ratio (as described with respect to other anchors, above), which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body/fibrous construct 4 that increases in width, thickness and/or diameter at deployment, it should be understood that the suture 2 can also play a role in the deployment of the anchor 400 even though the suture 2 may remain free to slide in some embodiments, and non-slidable in others (at least at a particular position or point in use) in relation to the anchor body 4. The suture 2 helps to position, align and support the anchor body 4 (as should be understood by a person of skill in the art in conjunction with a review of this disclosure).

In other words, the anchor body/fibrous construct 4 has two primary functions. First, it becomes a base for the suture 2 to slide within (within the column/lumen 6). Second, when compressed and/or pleated during deployment, the anchor body 4 becomes more compact in one direction thereby expanding outwardly and increasing its overall width, thickness or diameter to create a retention capacity. This action of having the anchor body 4 change in shape to increase its overall width, thickness or diameter is a useful characteristic which may be used advantageously to secure the anchor 400 in a hole 900 or against a bony or soft tissue. It is this combination of the expanding anchor body 4 coupled with the suture 2 remaining slidable (in some embodiments; and non-slidable in others, at least at a particular position or point in use) in relation to the anchor body 4 that render embodiments of the present invention ideal for the reattachment of soft tissue to bone or soft tissue to soft tissue where it is desirable to pass sliding knots to secure a repair.

In one embodiment, an inventive configuration, structure, and resulting function of a soft all-suture anchor that utilizes a hybrid combination of soft implantable materials is provided. A hybrid soft all-suture anchor of an embodiment includes superior pull-out strength properties as compared to conventional soft all suture anchors. Embodiments of the present invention provide a better soft all-suture anchor for use in hard bone, due in part to a hybrid expanding component portion. These embodiments are also suitable for use in soft cancellous bone where there is a very thin or weak cortical layer. The hybrid all-suture anchor can include, but is not limited to, an expandable member/portion configured to increase in size from a first pre-deployed condition to a second deployed condition upon the application of an activator; and a filament having a first filament end and a second filament end, and positioned in contacting relation to the expandable member in the second deployed condition. The anchor can also include a flat fibrous construct having a first end and a second end, and wherein the filament passes through the fibrous construct. The flat fibrous construct includes a first state in which the flat fibrous construct is uncompressed and extends along the longitudinal axis of the filament when in an unfolded and pre-deployed condition; and a second state in which the flat fibrous construct is compressed and expanded in a direction perpendicular to longitudinal axis of the filament in a deployed condition. The structure, configuration, and functionality of the expandable member, and of the fibrous construct (when part of an embodiment), help to set and hold the anchor in the bone hole in a post-deployment condition. The expandable portion/member can be part of a hybrid all-suture anchor used with any filament portion (as described herein) only. The expandable portion/member can also be part of a hybrid all-suture anchor used with any filament portion and any fibrous construct portion (as described herein).

Figure 31:
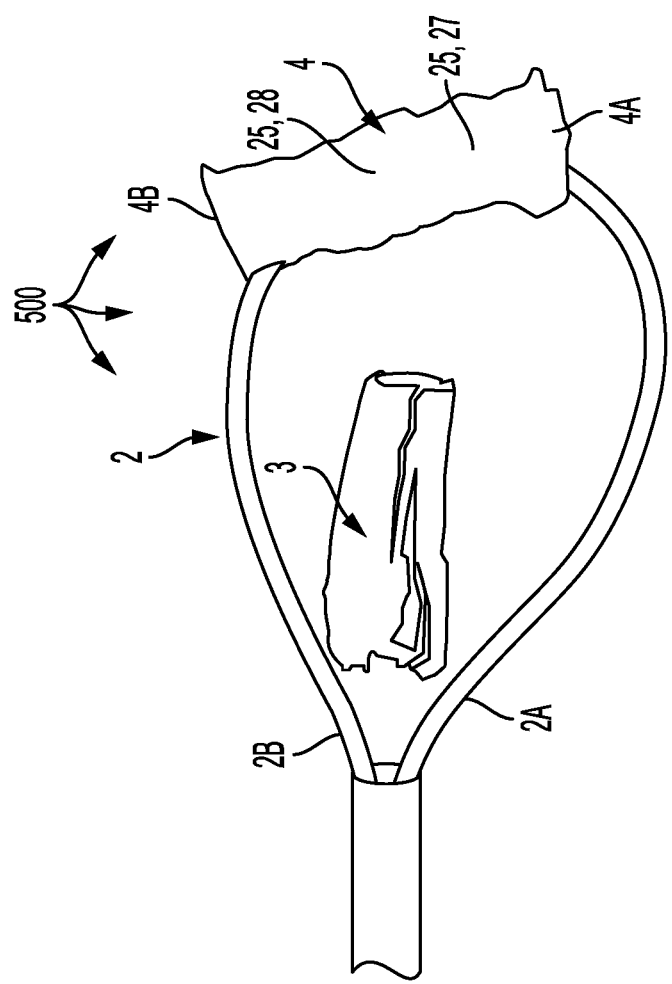
FIG. 31 is a perspective view digital photograph of a woven material in an unloaded (not loaded onto an installation device or inserter), pre-deployment configuration according to an alternative embodiment.

For example, referring to FIG. 31, a perspective view of a hybrid soft all-suture anchor 500 in a pre-deployment configuration, according to an embodiment is shown. The hybrid all-suture anchor 500 can include, but is not limited to, a flat fibrous construct 4 having a first end 4A, a second end 4B. A filament 2 is shown having a first end 2A and a second end 2B, and woven, threaded, or otherwise passing through the fibrous construct 4 at passing locations 25, 27 and 25, 28. See U.S. Pat. No. 9,826,971 for a further description of the structural aspects of the filament and fibrous construct, which is part of this example of the invention (as should be understood by a person of ordinary skill in the art in conjunction with a review of this disclosure).

In an embodiment, the filament 2 is free to slide through the fibrous construct 4 (and the expandable portion 3 when attached thereto) such that the filament 2 can be removed from the fibrous construct 4 from the first end 4A of the fibrous construct 4 and/or the second end 4B of the fibrous construct 4. In accordance with an alternative embodiment, the filament is locked and not slidable through the fibrous construct 4 and/or the expandable portion 3 (when attached to the expandable portion 3).

Figure 32:
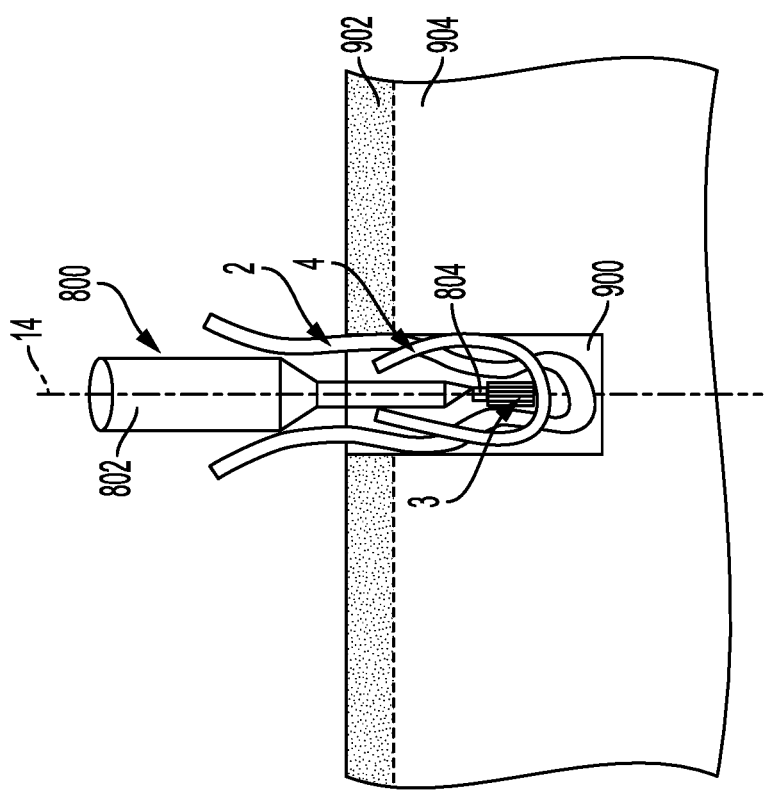
FIG. 32 is a side view schematic representation of an embodiment of the woven material of FIG. 31 connected to an installation device or driver in a pre-deployment configuration.
Figure 33:
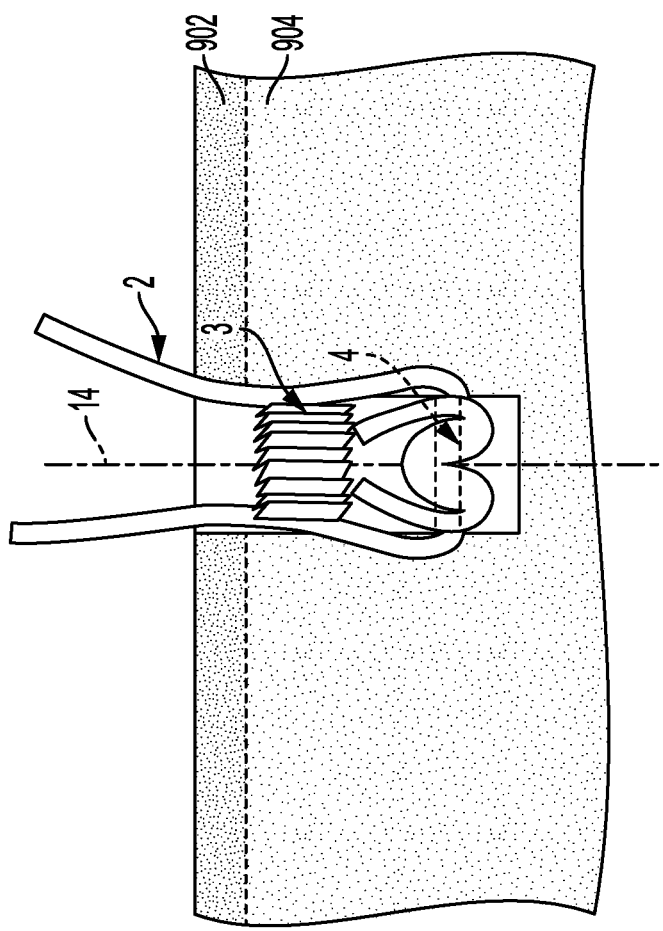
FIG. 33 is a side view schematic representation of an embodiment of the woven material of FIG. 31 in a post-deployment configuration positioned in a bone hole.
Figure 34:
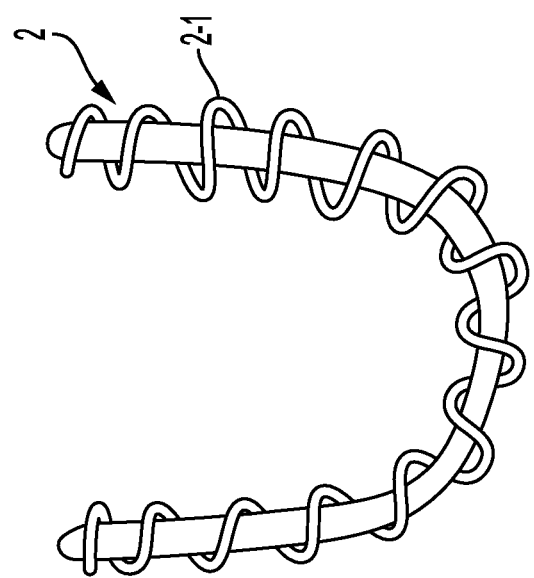
FIG. 34 is a side view schematic representation of a portion of a woven material according to an alternative embodiment.

Turning now to FIGS. 32 and 33, there are shown side view schematic representations of an embodiment of the all-suture anchor 500 in the pre-deployment and post-deployment configurations. As described above, the all-suture anchor 500 contains at least two sections: at least one suture 2 with a first end 2A and a second end 2B; and an anchor body/fibrous construct 4 with a first end 4A and a second end 4B, which is configured to form a portion of the anchor 500 that can increase in width, thickness and/or diameter and shrink in length as part of deployment. The all-suture anchor 500 also includes an expandable portion 3 which is configured to form a portion of the anchor 500 that can increase in size in the post-deployment configuration in response to an activator (as should be understood by a person of ordinary skill in the art in conjunction with a review of this disclosure).

As shown in FIG. 32, the installation device (or inserter, as described herein above) in the pre-deployment configuration is provided. The all-suture anchor 500 is shown connected to the distal deployment end 804 of an installation device 800 (which can be an inserter, as described herein above), which also includes a handle 802. The distal deployment end 804 and the all-suture anchor 500 are shown positioned in a bone hole 900 in cancellous bone 904 under the bone cortex 902. In order to deploy the all-suture anchor 500 (which can be connected to other tissue that needs to be brought into apposition to the bone, as should be understood by a person of ordinary skill in the art in conjunction with a review of this disclosure), the first end 2A and/or the second end 2B are pulled/tensioned in a direction away from the bone hole 400. The first end 2A and the second end 2B can be pulled/tensioned in a direction away from the bone hole 900 with or without the installation device 800 in place in the bone hole 900 (if installation device 800 is in place in the bone hole 900, it can act as a counter force to the tension force out of the hole 900 to assist with the deployment of the all-suture anchor 500). In addition, an activator can be added to the anchor to cause the expandable portion to expand to a second size greater than the first pre-deployment size. In one embodiment, the activator is water.

As shown in FIG. 33, the anchor body/fibrous construct 4 is shown "shortened" and "expanded" in the post-deployment configuration and locked in the bone hole 900, which can be additive to the increase due to pleats formed by the fibrous construct 4 (which may also be part of the fibrous construct 4). The all-suture anchor 500, and, in particular, the fibrous construct 4 takes advantage of Poisson's ratio (similarly, as discussed above), which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body/fibrous construct 4 that increases in width, thickness and/or diameter at deployment, it should be understood that the suture 2 can also play a role in the deployment of the anchor 500 even though the suture 2 may remain free to slide in some embodiments, and non-slidable in others (at least at a particular position or point in use) in relation to the anchor body 4. The suture 2 helps to position, align and support the anchor body 4 (as should be understood by a person of skill in the art in conjunction with a review of this disclosure).

In other words, the anchor body/fibrous construct 4 has two primary functions. First, it becomes a base for the suture 2 to slide within (within the column/lumen 6). Second, when compressed and/or pleated during deployment, the anchor body 4 becomes more compact in one direction thereby expanding outwardly and increasing its overall width, thickness or diameter to create a retention capacity. This action of having the anchor body 4 change in shape to increase its overall width, thickness or diameter is a useful characteristic which may be used advantageously to secure the anchor 500 in a hole 900 or against a bony or soft tissue. It is this combination of the expanding anchor body 4 coupled with the suture 2 remaining slidable (in some embodiments; and non-slidable in others, at least at a particular position or point in use) in relation to the anchor body 804 that render embodiments of the present invention ideal for the reattachment of soft tissue to bone or soft tissue to soft tissue where it is desirable to pass sliding knots to secure a repair.

Still referring to FIG. 33, the expandable portion 3 is shown in the expanded second size, greater than the first smaller pre-deployment size, after exposure to the activator. The expandable portion expands greatly in volume when exposed to the activator, causing it to wedge in the bone hole 900 and lock the anchor 500 in place. In accordance with an embodiment, in order to tension the filament 2 to reattach soft tissue (not shown), the filament 2 can freely slide backward and forward through the fibrous construct 4 and through the expandable portion 3 (as may be necessary when connected to the expandable portion 3). In certain situations without the presence of fibrous construct 4, the free sliding filament 2 could potentially cut through the expandable portion 3 resulting in a less than optimum deployment of the all-suture anchor 500. As such, in some embodiments of the all-suture anchor 500 with or without the fibrous construct 4, a second short length of suture 2-1 could be wrapped or looped around the filament 2 (see FIG. 34) to prevent sawing/cutting through the expandable portion 3 by the filament 2 when in contacting relation with the expandable portion 3.

Turning to FIG. 35, a side view digital photograph of an embodiment of the all-suture anchor of FIG. 31 in a post-deployment configuration after addition of an activator according to an embodiment is shown. As shown, the expandable portion 3 has increased in size to a second deployed structural condition (bone hole is not shown to illustrate the extent of expansion of expandable portion 3), and the filament 2 is positioned through and/or in otherwise contacting relation with the expandable portion 3.

Similarly with respect to the filament 2 and fibrous construct 4 described above and the embodiments shown in FIGS. 32-34, the expandable portion 3 can be a part of any all-suture anchor described herein or otherwise including the all-suture anchor shown and described in U.S. patent application Ser. No. 16/033,616. The same structure and functionality of the expandable portion 3 described above and shown in FIGS. 32-34 can apply to these embodiments of an all-suture anchor (with and without the fibrous construct).

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. An all-suture anchor, comprising:
   an anchor body having a first end and a second end, the second end folded toward the first end, creating a first limb extending to the first end and a second limb extending to the second end;
   wherein the anchor body is composed of a first material having a first density;
   a first piercing in the second limb;

wherein the first limb extends through the first piercing;

a passing filament having a pair of free ends, the passing filament woven through the anchor body at a plurality of passing locations such that one of the pair of free ends extends from the first end of the anchor body and the other of the pair of free ends extends from the second end of the anchor body;

wherein the passing filament is composed of a second material having a second density, and the second density is different than the first density; and wherein in an undeployed state, the anchor body has a first thickness and in a deployed state, the anchor body has a second thickness which is greater than the first thickness.

2. The all-suture anchor of claim 1, further comprising a second piercing in the second limb, wherein the first limb extends through the second piercing.

3. The all-suture anchor of claim 2, wherein the first limb and the second limb form a figure 8 pattern.

4. The all-suture anchor of claim 1, wherein the anchor body is composed of round suture.

5. The all-suture anchor of claim 1, wherein the anchor body is composed of flat suture.

6. The all-suture anchor of claim 1, wherein the anchor body is composed of an ultra-high-molecular-weight polyethylene braid.

7. The all-suture anchor of claim 1, wherein a passing section of the passing filament between two of the plurality of passing locations is on an outer surface of the anchor body.

8. The all-suture anchor of claim 1, wherein the passing filament is woven through the anchor body in a U-shaped pattern.

* * * * *